United States Patent
Smith et al.

(10) Patent No.: US 9,744,189 B1
(45) Date of Patent: *Aug. 29, 2017

(54) COMPOSITIONS OF LITHIUM SALTS AND METHODS OF USE

(71) Applicants: Adam J. Smith, Tampa, FL (US); R. Douglas Shytle, Largo, FL (US)

(72) Inventors: Adam J. Smith, Tampa, FL (US); R. Douglas Shytle, Largo, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/539,411

(22) Filed: Nov. 12, 2014

Related U.S. Application Data

(60) Provisional application No. 61/903,094, filed on Nov. 12, 2013.

(51) Int. Cl.
*A61K 33/00* (2006.01)
*A61K 47/12* (2006.01)

(52) U.S. Cl.
CPC .............. *A61K 33/00* (2013.01); *A61K 47/12* (2013.01)

(58) Field of Classification Search
CPC ................................. A61K 33/00; A61K 47/12
See application file for complete search history.

(56) References Cited

U.S. PATENT DOCUMENTS

| | | | | |
|---|---|---|---|---|
| 5,585,118 | A * | 12/1996 | Stoll | A61K 33/00 424/484 |
| 2014/0242193 | A1 | 8/2014 | Zaworotko et al. | |
| 2016/0052941 | A1 * | 2/2016 | Zaworotko | A61K 45/06 514/423 |

FOREIGN PATENT DOCUMENTS

WO    WO2012129568    *   9/2012  ............ A61K 33/14

OTHER PUBLICATIONS

Baldessarini, Ross J., et al., Treating the Suicidal Patient with Bipolar Disorder. Reducing Suicide Risk with Lithium. Ann N Y Acad Sci. Apr. 2001;932:24-38.
Beevers, A., et al., X-Ray Examination of Sucrose. Nature. Jun. 29, 1946;157:872.

(Continued)

*Primary Examiner* — Rachael Bredefeld
(74) *Attorney, Agent, or Firm* — Robert J. Varkonyi; Smith & Hopen, P.A.

(57) ABSTRACT

Lithium is regarded as the gold standard comparator and benchmark treatment for mania. One of the problems associated with Lithium is its narrow therapeutic window. Recent attempts to find new drugs with similar therapeutic activities have yielded new chemical entities. However, these potential new drugs have yet to match the many bioactivities attributable to lithium's efficacy for the treatment of neuropsychiatric diseases. Consequently, an intense effort for re-engineering lithium therapeutics using cocrystallization is currently underway. The evaluation of pharmacokinetics of previously unexplored lithium salts with organic anions (lithium salicylate and lithium lactate) has found that these lithium salts exhibit profoundly different pharmacokinetics compared to the more common FDA approved salt, lithium carbonate, in rats. Remarkably, lithium salicylate produced elevated blood and brain levels of lithium beyond 48 hours post-dose without the sharp peak that contributes to the toxicity problems of current lithium therapeutics.

15 Claims, 9 Drawing Sheets

(56) References Cited

OTHER PUBLICATIONS

Braga, Dario, et al., Combining piracetam and lithium salts: ionic co-crystals and co-drugs? Chem Comm (Camb). Aug. 25, 2012;48, 8219-8221.

Davenport VD. Distribution of parenterally administered lithium in plasma, brain and muscle of rats. Am J Physiol. 1950; 163:633-641.

Ebadi, Manuchair S., et al. Pharmacokinetics of Lithium and its Regional Distribution in Rat Brain. Eur J Pharmacol. 1974; 27:324-329.

Goodwin, Frederick K., et al., Suicide Risk in Bipolar Disorder During Treatment with Lithium and Divalproex. JAMA. Sep. 17, 2003;290(11):1467-1473.

Lippmann, Steven, et al. A Comparison of Three Types of Lithium Release Preparations. Hosp Community Psychiatry. Feb. 1983;34(2):113-114.

Smith, D.F., Lithium Orotate, Carbonate and Chloride: Pharmacokinetics, Polydipsia and Polyuria in Rats. B J Pharmac. Apr. 1976;56(4):399-402.

Smith, Adam J., et al. Cocrystals of Quercetin with Improved Solubility and Oral Bioavailability. Molecular Pharmaceutics, 2011; 8, 1867-1876.

Smith, Adam J., et al., Improving Lithium Therapeutics by Crystal Engineering of Novel Ionic Cocrystals. Mol Pharm. Dec. 2, 2013;10(12):4728-38.

Thies-Flechtner, K, et al., Effect of Prophylactic Treatment on Suicide Risk in Patients with Major Affective Disorders. Data from a Randomized Prospective Trial. Pharmacopsychiatry. May 1996;29(3):103-107.

Wouters, Johan, et al., Novel Pharmaceutical Compositions through Co-crystallization of Racetams and Li+ Salts. CrystEngComm, 2013, 15, 8898-8902.

Timmer, Richard T, et al., Lithium Intoxication. J Am Soc Nephrol. Mar. 1, 1999;10(3):666-674.

Vismari Luciana, et al., Bioavailability of Immediate and Controlled Release Formulations of Lithium Carbonate. Rev Bras Psiquatr. 2002;24(2):74-79.

Lithium—FDA prescribing information, side effects and uses. https://www.drugs.com/pro/lithium.html. Accessed on Aug. 29, 2016.

Lithium: The Test. Lab Tests Online. Https://labtestsonline.org/understanding/analytes/lithium/tab/tester. Accessed on Aug. 29, 2016.

* cited by examiner

COMPOSITIONS OF LITHIUM SALTS AND METHODS OF USE

CROSS-REFERENCE TO RELATED APPLICATION

This application claims priority to U.S. Provisional Patent Application No. 61/903,094, entitled "Blood and Brain Pharmacokinetics of Previously Unexplored Lithium Salts", filed on Nov. 12, 2013, the contents of which are herein incorporated by reference.

FIELD OF INVENTION

This invention relates to pharmaceutical compositions and methods of treating neurological diseases. Specifically, the invention provides for novel lithium cocrystals and uses of lithium salts and cocrystals in treatment of neurological disease.

BACKGROUND OF THE INVENTION

Lithium is one of the oldest psychiatric drugs in existence. Lithium salt compositions, including lithium carbonate ($Li_2CO_3$) lithium citrate ($Li_3C_6H_5O_7$), are commonly used lithium compounds prescribed for treatment. Lithium is commonly used to treat bipolar disorder and acute mania, mania (DSM-II and DSM-III). Lithium is also used for other disorders, such as depression, schizophrenia, epilepsy, for eating disorders, including anorexia and bulimia, cyclical vomiting, and alcoholism. It has also been used for anemia and neutropenia, liver disease, kidney disorders, thyroid adjustment, Huntington's disease, Grave's disease, Tourette's syndrome, and in some cases of attention deficit-hyperactivity disorder.

Alternative lithium salts that have been proposed for use include lithium orotate ($C_5H_3LiN_2O_4$), lithium bromide (LiBr) and lithium chloride (LiCl). However, it was found that lithium bromide and lithium chloride are toxic. Further, other salts, such as lithium fluoride (LiF) and lithium iodide (LiI), are assumed to toxic and have not been tested. This is further complicated by the fact that lithium compounds have a small therapeutic window, with the U.S. National Library of Medicine providing a therapeutic range of 0.8 to 1.2 mEq/L. On administration, lithium generally reaches peak plasma levels at 30 minutes to 2 hours, though peak plasma levels after overdoses can take 72 hours (Timmer & Sands, Lithium intoxication. J Am Soc Nephrol. 1999 Mar. 1; 10(3):666-74). CNS levels of lithium are approximately 40% of plasma levels due to active transport of lithium out of the CNS, and levels peak about 24 hours after plasma levels peak (Timmer & Sands, Lithium intoxication. J Am Soc Nephrol. 1999 Mar. 1; 10(3):666-74). The drug elimination half-life is 24 hours for acute treatment, and can vary to 60 hours for some chronically treatment individuals (Timmer & Sands, Lithium intoxication. J Am Soc Nephrol. 1999 Mar. 1; 10(3):666-74). Typically serum levels greater than 1.5 mEq/l increase the likelihood of toxicity and detrimental effects while levels of 2.0 or higher are considered toxic (U.S. National Library of Medicine).

Lithium toxicity can present as drowsiness, course muscle tremors or weakness, nausea, seizures, problems with muscle control, such as speaking, eye control, or locomotor control, vomiting, diarrhea, coma and death. Toxicity also affects cerebral function, and can cause neuropathy, as well as heart abnormalities.

Therapeutic levels of lithium interact with various neurotransmitters and receptors, causing decreases in norepinephrine (noradrenaline) release and increasing serotonin synthesis. In vitro, rat serotonergic neuron cultures treated with lithium resulted in serotonin release during a depolarization compared to no lithium treatment and the same depolarization. Other studies have shown lithium may interact with nitric oxide (NO) signaling in the central nervous system, which plays a crucial role in the neural plasticity, and lithium inhibits inositol monophosphatase that results in higher inositol triphosphate. Due to the pharmacological effects of lithium, as well as its bioactivity, the drug remains heavily utilized by clinicians today despite intense marketing of newer alternative drugs that do not contain the toxicity issues that require frequent blood monitoring by a clinician.

Long-term lithium therapy has been linked to altered kidney functioning, resulting in reduced capacity of renal concentrating ability, and occasionally nephrogenic diabetes insipidus, with polyuria and polydipsia. Some studies have linked reduction in kidney functioning to morphological changes in the nephrons.

Recently, there have been efforts to find a "lithium mimetic" with improved safety (Singh, et al., A safe lithium mimetic for bipolar disorder. Nat Commun. 2013 Jan. 8; 4:1332; Gould & Manji, Glycogen synthase kinase-3: a putative molecular target for lithium mimetic drugs. Neuropsychopharmacology. 2005 July; 30(7):1223-37). For example, such as ebselen which inhibits inositlol monophosphatase to produce a lithium-like response in mouse models (Singh, et al., A safe lithium mimetic for bipolar disorder. Nat Commun. 2013 Jan. 8; 4:1332). Alternatively, others have used crystal engineering techniques to re-engineer lithium therapeutics by creating novel ionic cocrystals of lithium salts (Smith et al., Reinventing lithium therapeutics by crystal engineering of novel ionic cocrystals. Mol Pharm. 2013 Dec. 2; 10(12):4728-38; Braga et al., Combining piracetam and lithium salts: ionic co-crystals and co-drugs? Chem Commun (Camb). 2012 Aug. 25; 48(66):8219-21; Wouters, et al., Novel Pharmaceutical Compositions through Co-crystallization of Racetams and Li+ Salts. Cryst Eng Comm. 2013 Aug. 2, 15:8898-8902). Cocrystallization represents a low risk, low cost approach with the most potential for achieving the desired therapeutic outcome for many reasons. For example, the active pharmaceutical ingredient (API) in this crystal engineering approach remains lithium, which is already FDA approved with a long history of use in medicine. Furthermore, the FDA has just released draft guidance for industry regarding the regulation of pharmaceutical cocrystals that includes an expedited pathway for their approval (FDA. April 2013. Guidance for Industry: Regulatory Classification of Pharmaceutical Co-Crystals. In Services UDoHaH, Administration FaD, Research CfDEa, editors., ed.). Thus, the cost to bring a lithium cocrystal drugs to market will likely be significantly lower than that of a new drug. However, none of these chemical entities have matched lithium's polypharmacological mechanisms of action for the treatment of neuropsychiatric diseases. Because lithium is so effective at treating neuropsychiatric diseases such as bipolar disorder and suicidality (Baldessarini, et al., Treating the suicidal patient with bipolar disorder. Reducing suicide risk with lithium. Ann N Y Acad Sci. 2001 April; 932:24-38; Goodwin, et al., Suicide risk in bipolar disorder during treatment with lithium and divalproex. JAMA. 2003 Sep. 17; 290(11):1467-73; Thies-Flechtner, et al., Effect of prophylactic treatment on suicide risk in patients with major affective disorders. Data from a randomized prospective trial. Pharmacopsychiatry. 1996

May; 29(3):103-7) it is still considered the gold standard for treatment of mania, despite known toxicity issues that require frequent blood monitoring by a clinician.

Consequently there exists a need to re-engineer lithium therapeutics, such as through use of cocrystallization, to improve pharmacokinetics, and optimizing safety and efficacy. Accordingly, what is needed is a method for treating a neurological disorder using a novel ionic cocrystals of lithium salts where the anion of the lithium salt is pharmaceutically acceptable and contains appropriate blood and brain pharmacokinetics.

SUMMARY OF THE INVENTION

Often, lithium salts are assumed to dissociate following oral administration leading to very similar blood and brain levels of lithium. In fact, one study compared lithium carbonate, lithium chloride, and lithium orotate in rats (Smith, 1976. Lithium orotate, carbonate and chloride: pharmacokinetics, polyuria in rats. B J Pharmacol. 1976 April; 56(4):399-402). The study found no differences in the uptake, distribution, and excretion of the lithium ion. Still, due to the complex nature of the pharmacokinetics of multi-component materials, an evaluation of the blood and brain pharmacokinetics was conducted for two previously unexplored salts of lithium, lithium salicylate, seen in FIG. 1(a), and lithium lactate, seen in FIG. 1(b).

A composition of a lithium salt, preferably an organic anion salt of lithium, and a complementary neutral organic compound are combined in a stoichiometric ratio. The cocrystal has the formula LiX.aM, wherein X is salicylate or lactate, M is a neutral organic molecule, and a is from 0.5 to 4. In specific variations of the invention, the lithium salicylate or lithium lactate has a molar ratio to the organic molecule of 1:1 or 1:2. Optionally, the organic molecule is an amino acid, synthetic amino acid, xanthine, polyphenol, or sugar. In general, organic anion lithium ionic cocrystal compositions of the present invention may be prepared by combining the lithium salt and the complementary organic compound (i.e., the cocrystal precursor) in a solvent and using a commonly used method to promote crystallization such as evaporating or cooling the solvent to form the cocrystals.

Examples of amino acids or synthetic amino acids are alanine, arginine, asparagine, aspartic acid, cysteine, isoleucine, glutamic acid, glutamine, glycine, histidine, leucine, lysine, methionine, phenylalanine, proline, selenocysteine, serine, taurine, threonine, tryptophan, tyrosine, nicotinic acids, and valine. By way of further example, the amino acid is an L-amino acid such as L-phenylalanine, L-leucine, or L-tyrosine. In an alternative embodiment, the amino acid is a D-amino acid such as D-phenylalanine, D-leucine, or D-tyrosine. In an alternative embodiment, the cocrystal precursor comprises a non-proteinogenic amino acid. Synthetic amino acids can include the naturally occurring side chain functional groups or synthetic side chain functional groups which modify or extend the natural amino acids with alkyl, substituted alkyl, cycloalkyl, heterocyclic, substituted heterocyclic, aryl alkyl, aryl, heteroaryl, heteroaryl alkyl, and like moieties as framework and with carboxyl, amine, hydroxyl, phenol, carbonyl, or thiol functional groups; exemplary synthetic amino acids include β-amino acids and homo or β-analogs of natural (standard) amino acids. Other exemplary amino acids include pyrrolysine, betaine, and carnitine.

Examples of xanthine are caffeine, paraxanthine, theophylline, and threobromine.

Examples of polyphenols can be classified into the following categories: (1) phenolic acids, (2) flavonoids, (3) stilbenoids; (4) tannins, (5) monophenol such as hydroxytyrosol or p-tyrosol, (6) capsacin and other capsaicinoids and (7) curcumin. Phenolic acids form a diverse group including, for example, (a) hydroxycinnamic acids, e.g., p-coumaric acid, caffeic acid, and ferulic acid; (b) hydroxybenzoid acids, e.g., p-hydroxybenzoic acid, gallic acid, and ellagic acid; and (c) rosmarinic acid. Tannins are large molecules, found in red wine, tea, and nuts; the term is applied to any large polyphenolic compound containing sufficient hydroxyls and other suitable groups (such as carboxyls) to form strong complexes with proteins and other macromolecules and are usually divided into hydrolyzable tannins and condensed tannins (proanthocyanidins). At the center of a hydrolyzable tannin molecule, there is a polyol carbohydrate (usually D-glucose); the hydroxyl groups of the carbohydrate are partially or totally esterified with phenolic groups such as gallic acid (in gallotannins) or ellagic acid (in ellagitannins).

Flavonoids are a long and well-known class of natural product that is attracting increasing attention as nutraceuticals and pharmaceuticals. Flavonoids are based upon a group of compounds called chalcones and typically contain a 3-ring structure called flavone. The metabolic pathway in plants affords many derivatives including flavonols, flavan-3-ols, tannins and other polyphenolics. Flavonoids are synthesized and widely distributed in plants and fulfill many functions including pigmentation in flowers, and protection from attack by microbes and insects. The widespread distribution of flavonoids means that they are ingested in significant quantities by animals. Furthermore, their variety, their relatively low toxicity compared to, for example, alkaloids, and their biological activity (they can be antiallergic, anti-inflammatory, anti-microbial, anti-cancer and they can improve cognitive functions) means that consumers, food manufacturers and pharmaceutical companies have become interested in flavonoids for their medicinal properties. Indeed, the beneficial effects of fruit, vegetables, and tea or even red wine have been attributed to flavonoid compounds. Although many flavonoids are abundant and commercially available they can be hard to purify and crystallize and their solubility can be low. In one embodiment, therefore, the flavonoids are resveratrol, epigallocatechin-3-gallate (EGCG), quercetin, ferulic acid, ellagic acid, hespereten, and protocatechuic acid. In specific examples, the flavonoid selected from the group consisting of EGCG, ferulic acid, ellagic acid, hespereten, and protocatechuic acid.

In embodiments where the sugar as the organic molecule is a sugar, the sugar can include monosaccharides and disaccharides. For example, the sugar can be fructose, galactose, glucose, lactitol, lactose, maltitol, maltose, mannitol, melezitose, myoinositol, palatinite, raffinose, stachyose, sucrose, trehalose, or xylitol.

In specific variations of the invention, the composition optionally includes one or more nutraceuticals, such as one of the previously mentioned flavonoid or a nutraceutical currently believed to possess biological activity. For example, in this embodiment, the nutraceutical may be selected from the group consisting of vitamin B2 (riboflavin), glucosamine HCI, chlorogenic acid, lipoic acid, catechin hydrate, creatine, acetyl-L-carnitine HCI, vitamin B6, pyridoxine, caffeic acid, naringenin, vitamin B1 (thiamine HCI), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, resveratrol, epigallocatechin-3-gallate (EGCG), quercetin, ferulic acid, ellagic acid, hespereten, and protocatechuic acid. By way of further example, in this embodiment, the nutraceutical may be selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, quercetin, ferulic acid, ellagic acid, hespereten, and protocatechuic acid.

In one embodiment, the lithium salt and the complementary neutral organic compound are combined in an aqueous system. Although not necessarily preferred, the lithium salt and complementary neutral organic compound may be dissolved in polar organic solvents such as acetone, acetonitrile, DMSO and alcohols.

In one embodiment, organic anion lithium ionic cocrystal compositions or the present invention may be prepared by combining a lithium-containing compound, an organic acid, and a complementary neutral organic compound, in a solvent, such as water, and using a commonly used method to promote crystallization such as evaporating or cooling the solvent.

The invention also includes methods for treating a neurological disorder by administering a therapeutically effective amount of a composition to a patient in need thereof, wherein the composition further comprises lithium salicylate or lithium lactate. Optional neurological disorders include bipolar disorder, acute mania, manic depression, schizophrenia, anorexia, bulimia, Tourette's syndrome, cyclical vomiting, paresthesias, or aggressive behavior in attention deficit hyperactivity disorder. In specific embodiments, the composition is administered as a cocrystal formulation, as discussed in the preceding paragraphs.

Adult doses of the composition vary based on the disease and regularity of administration. However, the present compounds permit longer duration with lower peak levels of lithium in the blood and brain, as discussed below. Examples of adult doses for are between 15 mg/kg/day to 200 mg/kg/day. Pediatric doses are between 15 mg/kg/day to 100 mg/kg/day. For example, a dose of the composition can be 15 mg/kg/day, 20 mg/kg/day, 25 mg/kg/day, 30 mg/kg/day, 40 mg/kg/day, 45 mg/kg/day, 50 mg/kg/day, 60 mg/kg/day, 65 mg/kg/day, 70 mg/kg/day, 75 mg/kg/day, 80 mg/kg/day, 85 mg/kg/day, 90 mg/kg/day, 100 mg/kg/day, 110 mg/kg/day, 120 mg/kg/day, 125 mg/kg/day, 130 mg/kg/day, 140 mg/kg/day, 150 mg/kg/day, 155 mg/kg/day, 160 mg/kg/day, 170 mg/kg/day, 175 mg/kg/day, 180 mg/kg/day, 190 mg/kg/day, or 200 mg/kg/day. As the compositions provided for extended lithium half-life, the compositions can also be administered every other day, or every third day. In such situations, the doses are adjusted according to the daily dosing regimen as would be apparent to one of skill in the art. For example, where a dose of 40 mg/kg/day are indicated, the dose would be administered at 80 mg/kg for quaque alternis die administration, i.e. for dosing every other day.

The invention also includes methods for treating a disorder, where the disorder is bipolar disorder, acute mania, manic depression, schizophrenia, anorexia, bulimia, Tourette's syndrome, cyclical vomiting, paresthesias, aggressive behavior in attention deficit hyperactivity disorder, Meniere's disease, anemia, neutropenia, headache, alcoholism, epilesy, diabetes, liver disease, kidney disorders, arthritis, seborrhea, overactive thyroid, asthma, Huntington's disease, Grave's disease, herpes simplex infection, or tardive dyskinesia. The method comprises administering a therapeutically effective amount of a composition to a patient in need thereof, wherein the composition further comprises lithium salicylate or lithium lactate. In specific embodiments, the composition is administered as a cocrystal formulation, as discussed in the preceding paragraphs.

Adult doses of the composition vary based on the disease and regularity of administration. However, the present compounds permit longer duration with lower peak levels of lithium in the blood and brain, as discussed below. Examples of adult doses for are between 15 mg/kg/day to 200 mg/kg/day. Pediatric doses are between 15 mg/kg/day to 100 mg/kg/day. For example, a dose of the composition can be 15 mg/kg/day, 20 mg/kg/day, 25 mg/kg/day, 30 mg/kg/day, 40 mg/kg/day, 45 mg/kg/day, 50 mg/kg/day, 60 mg/kg/day, 65 mg/kg/day, 70 mg/kg/day, 75 mg/kg/day, 80 mg/kg/day, 85 mg/kg/day, 90 mg/kg/day, 100 mg/kg/day, 110 mg/kg/day, 120 mg/kg/day, 125 mg/kg/day, 130 mg/kg/day, 140 mg/kg/day, 150 mg/kg/day, 155 mg/kg/day, 160 mg/kg/day, 170 mg/kg/day, 175 mg/kg/day, 180 mg/kg/day, 190 mg/kg/day, or 200 mg/kg/day. As the compositions provided for extended lithium half-life, the compositions can also be administered every other day, or every third day. In such situations, the doses are adjusted according to the daily dosing regimen as would be apparent to one of skill in the art. For example, where a dose of 40 mg/kg/day are indicated, the dose would be administered at 80 mg/kg for quaque alternis die administration, i.e. for dosing every other day.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1A:
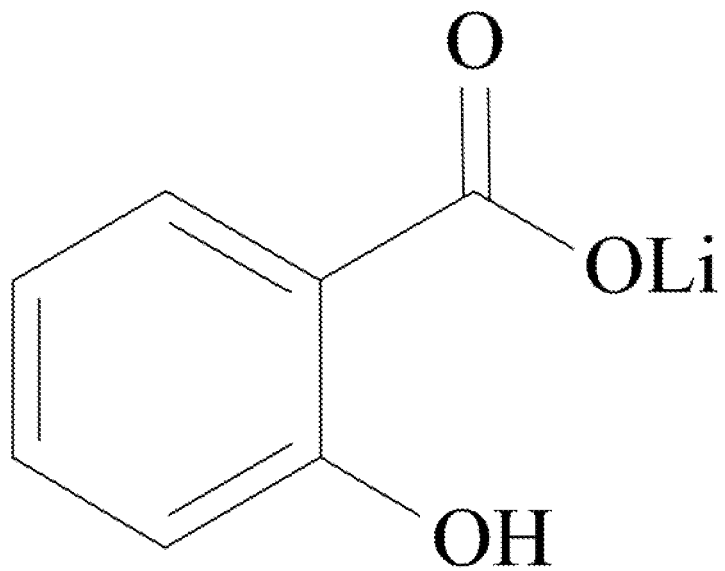
FIG. 1(a) depicts the chemical structure of lithium salicylate.
Figure 1B:
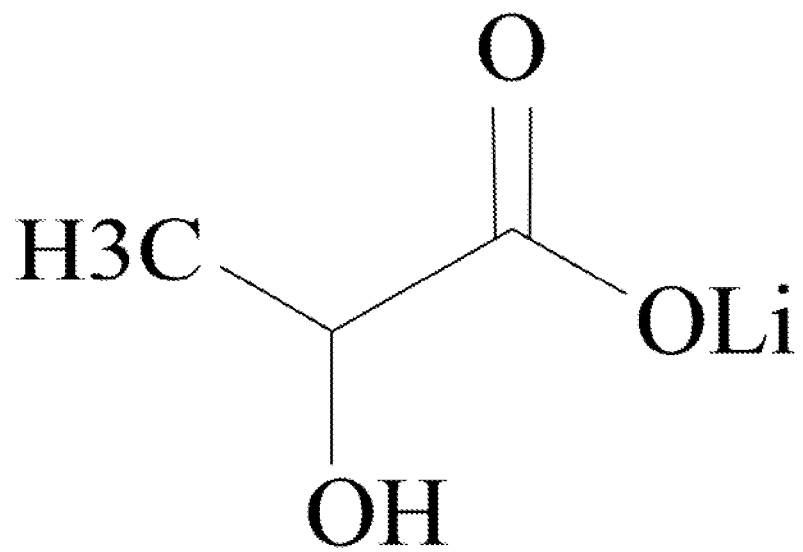
FIG. 1(b) depicts the chemical structure of lithium lactate.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention is a composition and method for treating a neurological disorder based on certain lithium salts possessing unique pharmacokinetic profiles, as well as re-engineered lithium therapeutics of these lithium salts using cocrystallization. The novel compound comprises at least one lithium salt selected from the group consisting of lithium salicylate and lithium lactate. The method for treatment comprises administering a compound comprising at least one lithium salt selected from the group consisting of lithium salicylate, lithium lactate, a cocrystal of lithium salicylate, and a cocrystal of lithium lactate. The invention also provides for novel cocrystal compounds of lithium salicylate and lithium lactate.

An "amino acid" as used herein refers to a molecule containing an amine group, a carboxylic acid group and a side-chain that varies between different amino acids.

A "cocrystal" as used herein refers to a multiple component crystal containing two or more non-identical compounds (cocrystal precursors) in a stoichiometric ratio (1:1) or a ratio of (2:1), each of which is solid under ambient conditions (i.e., 22° C., 1 atmosphere of pressure) when in their pure form.

A "neutral" composition as used herein refers to a composition, or moiety, optionally possessing both cationic and anionic groups, having a zero net electrical charge.

An "organic acid" as used herein is an organic Bronsted acid.

An "organic anion" as used herein is a conjugate base of an organic acid.

A "weak organic acid" as used herein refers to an organic Bronsted acid having a pKa of about 0 to about 10.

A "zwitterion compound" or "zwitterionic composition" as used herein refers to a macromolecule, material, or moiety, possessing cationic and anionic groups, or acidic and basic centers that tautomerize to the corresponding cationic and anionic groups. Typically, and preferably in the context of the present invention, these charged groups are balanced, resulting in a material with zero net electrical charge.

Pharmaceutical compositions of the present invention may comprise the active agent, i.e., a compound or composition comprising the organic anion lithium ionic cocrystal and a neutral organic compound in a stoichiometric ratio, alone or may include the active agent and any suitable additional component, such as one or more pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Each carrier is preferably acceptable in the sense of being compatible with the other ingredients of the formulation and not injurious to the patient.

Dosage unit forms of a pharmaceutical composition of the present invention comprise a desired amount of the active agent per dose unit and, if intended for oral administration, can be in the form, for example, of a tablet, a caplet, a pill, a hard or soft capsule, a lozenge, a cachet, a dispensable powder, granules, a suspension, an elixir, a dispersion, or any other form reasonably adapted for such administration. If intended for parenteral administration, it can be in the form, for example, of a suspension or transdermal patch. If intended for rectal administration, it can be in the form, for example, of a suppository. In one embodiment, the dosage unit form is a discrete dose form such as a tablet or a capsule suitable for oral administration, each containing a predetermined amount of the active agent.

Excipients employed in the compositions of the present invention may be solids, semi-solids, liquids or combinations thereof. In one embodiment, the excipient(s) is/are solids. Compositions of the invention containing excipients can be prepared by any known technique that comprises, for example, admixing an excipient with the cocrystal.

Compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, may constitute in total about 5% to about 99%, about 10% to about 85%, or even about 20% to about 80%, of the total weight of the composition. The carrier, carriers, diluent, or diluents selected may exhibit suitable flow properties and, where tablets are desired, compressibility.

Compositions of the invention optionally comprise one or more pharmaceutically acceptable disintegrants as excipients, particularly for tablet formulations. Suitable disintegrants include, but are not limited to, either individually or in combination, starches, including sodium starch glycolate {e.g., Explotab™ of PenWest) and pregelatinized corn starches {e.g., National™ 1551 of National Starch and Chemical Company, National™ 1550, and Colorcon™ 1500), clays {e.g., Veegum™ HV of R. T. Vanderbilt), celluloses such as purified cellulose, microcrystalline cellulose, methylcellulose, carboxymethylcellulose and sodium carboxymethylcellulose, croscarmellose sodium (e.g., Ac- Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, may constitute in total about 0.2% to about 30%, about 0.2% to about 10%, or even about 0.2% to about 5%, of the total weight of the composition.

Pharmaceutical compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a cocrystal of the present invention once the salt has been dissolved in a solution. Exemplary binding agents and adhesives include, but are not limited to, either individually or in combination, acacia; tragacanth; sucrose; gelatin; glucose; starches such as, but not limited to, pregelatinized starches (e.g., National™ 151 1 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, may constitute in total about 0.5% to about 25%, about 0.75% to about 15%, or even about 1% to about 10%, of the total weight of the pharmaceutical composition.

Many of the binding agents are polymers comprising amide, ester, ether, alcohol or ketone groups and, as such, are optionally included in pharmaceutical compositions of the present invention. Exemplary binding agents include polyvinylpyrrolidones such as povidone K-30. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Compositions of the invention optionally comprise one or more pharmaceutically acceptable wetting agents as excipients. Such wetting agents may be selected to maintain the cocrystal in close association with water, a condition that may improve bioavailability of the composition. Such wetting agents can also be useful in solubilizing or increasing the solubility of crystals.

Pharmaceutical compositions according to the present invention include formulations suitable for oral, rectal, intranasal, topical (including transdermal, buccal and sublingual), vaginal, parental (including subcutaneous, intramuscular, intravenous and intradermal) and pulmonary administration. The formulations can conveniently be presented in unit dosage form and can be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with a suitable carrier, such as liquid carriers or finely divided solid carriers or both, and then if necessary shaping the product. Formulations of the subject invention suitable for oral administration can be presented as discrete units such as capsules, cachets or tablets, each containing a predetermined amount of the active ingredient; or as an oil-in-water liquid emulsion, water-in-oil liquid emulsion, or as a supplement within an aqueous solution, for example, a tea. The active ingredient can also be presented as bolus, electuary, or paste.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; mouthwashes comprising the active ingredient in a suitable liquid carrier; and chocolate comprising the active ingredients.

Formulations suitable for topical administration according to the subject invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents. Topical formulations preferably comprise compounds that facilitate absorption of the active ingredients through the skin and into the bloodstream.

Formulations suitable for intranasal administration, wherein the carrier is a solid, include a coarse powder having a particle size, for example, in the range of about 20 to about 500 microns, which is administered in the manner in which snuff is taken, e.g., by rapid inhalation through the nasal passage from a container of the powder held close up to the nose. Suitable formulations wherein the carrier is a liquid for administration by nebulizer, include aqueous or oily solutions of the agent. Formulations may optionally comprise compounds that facilitate absorption of the active ingredients through the skin and into the bloodstream.

Formulations suitable for parenteral administration include aqueous and non-aqueous isotonic sterile injection solutions which can contain antioxidants, buffers, bacteriostats and solutes which render the formulation isotonic with the blood of the intended recipient; and aqueous and non-aqueous sterile suspensions which can include suspending agents and thickening agents, and liposomes or other microparticulate systems which are designed to target the compound to blood components or one or more organs. The formulations can be presented in unit-dose or multi-dose or multi-dose sealed containers, such as for example, ampoules and vials, and can be stored in a freeze-dried (lyophilized) condition requiring only the addition of the sterile liquid carrier, for example, water for injections, immediately prior to use. Extemporaneous injection solutions and suspensions can be prepared from sterile powders, granules and tablets of the kind previously described.

It should be understood that in addition to the ingredients particularly mentioned above, the formulations useful in the present invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Various delivery systems are known in the art and can be used to administer a therapeutic agent or composition of the invention, e.g., encapsulation in liposomes, microparticles, microcapsules, receptor-mediated endocytosis and the like. Methods of administration include, but are not limited to, parenteral, intra-arterial, intramuscular, intravenous, intranasal, and oral routes. The pharmaceutical compositions can be provided in the form of tablets, lozenges, granules, capsules, pills, ampoule, suppositories or aerosol form. The pharmaceutical compositions can also be provided in the form of suspensions, solutions, and emulsions of the active ingredient in aqueous or non-aqueous diluents, syrups, granulates or powders.

Pharmaceutical formulations of the invention can be administered simultaneously or sequentially with other drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids.

Preferred unit dosage formulations are those containing a daily dose or unit, daily subdose, or an appropriate fraction thereof, of an agent. Therapeutic amounts can be empirically determined and will vary with the condition being treated, the subject being treated, and the efficacy and toxicity of the agent. Similarly, suitable dosage formulations and methods of administering the agents can be readily determined by those of ordinary skill in the art.

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Male Sprague Dawley rats weighing 200-250 grams were housed in a vivarium with a 12 hour light-dark cycle. The rats were allowed to acclimate for a period of one week before any experiments were carried out, and were allowed free access to food and water throughout the experiment. The rats were dosed via oral gavage with 4 mEq/kg lithium salicylate (≥98% purity; Aldrich Corporation, St. Louis, Mo., USA) or lithium lactate (≥95% purity; Aldrich Corporation, St. Louis, Mo., USA) dissolved in deionized water. Chemical structures are shown in FIGS. 1(a) and (b).

Animals in each treatment group were euthanized at 2, 24, 48, and 72 hours (n=3/time point) and blood was collected by cardiac puncture and carefully perfused with a pressure-controlled pump to maintain microvasculature integrity before removing brain tissue. Blood was centrifuged at 1600×g at room temperature for 10 minutes and plasma was separated. A 500 µl aliquot was diluted 10 fold in a 5% TCA and 10% IPA solution, vortexed and allowed to sit for 10 minutes in order to precipitate proteins. These aliquots were centrifuged at 3000×g for 30 minutes and the supernatant was transferred to clean tubes prior to measuring lithium content using atomic absorption spectroscopy (AAS). Brains were rinsed with PBS, weighed, and an equal volume of concentrated $HNO_3$ was added. The brains were heated in nitric acid solution for 1 hour, allowed to cool to room temperature, then centrifuged at 3000×g for 1 hour. The supernatant was removed and diluted 10 fold in 10% IPA prior to measuring lithium content using AAS.

Phoenix WinNonlin® Version 6.3 (Pharsight, Certara, L.P., St. Louis, Mo.) was used to conduct a noncompartmental analysis of the pharmacokinetic data and generate the pharmacokinetic parameters in Table 1, shown below. The reported parameters include $C_{MAX}$, $T_{MAX}$, area under curve (AUC), and apparent terminal half-life (HL_Lambda_z).

TABLE 1

Pharmacokinetic Parameters of lithium salicylate or lithium lactate administered to rats.

|  | Lithium Salicylate | | Lithium Lactate | |
| --- | --- | --- | --- | --- |
|  | Blood | Brain | Blood | Brain |
| $T_{MAX}$ (hour) | 24 | 48 | 24 | 24 |
| $C_{MAX}$ (µg/mL or µg/g) | 2.21 | 2.89 | 4.54 | 3.87 |
| $AUC_{(0-72)}$ (hour * µg/mL or /g) | 121.8 | 153.1 | 157.2 | 152.0 |
| HL_Lambda_z (hour) | 19.3 | 23.2 | 6.9 | 13.0 |

Lithium was measured using atomic absorption spectroscopy (AAS) (Shimadzu AA-6200; Shimadzu Scientific Instruments, Inc., Columbia, Md.). Peak height measurements were carried out referring to values obtained for standards of known concentrations. Lithium measurements were plotted using GraphPad PRISM software (GraphPad Software, Inc., La Jolla, Calif.) as mean±SEM and two tailed t-tests were used to assess the statistical significance at each time point for the pharmacokinetic curves. The criterion for rejection of the null hypothesis was $p<0.05$.

Figure 2:
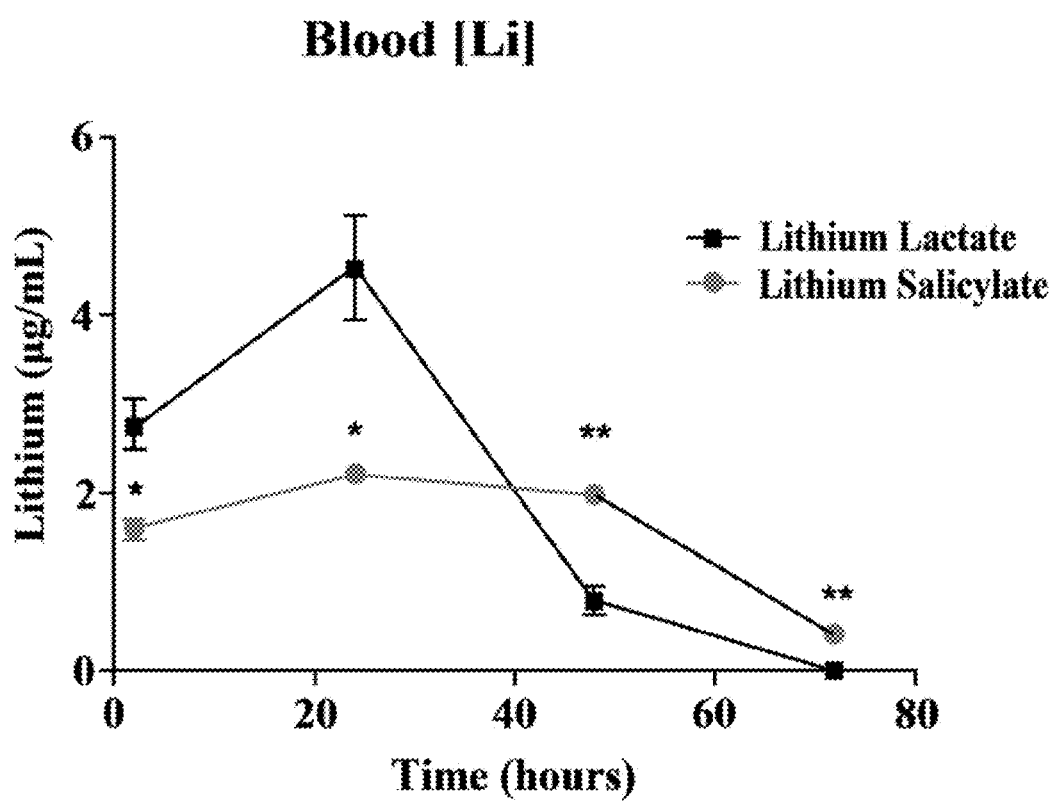
FIG. 2 is a graph showing plasma pharmacokinetics curves of lithium after administration of lithium lactate or lithium salicylate plotted as mean±SEM ($*p<0.05$, $p<0.01$, $*p<0.001$).
Figure 3:
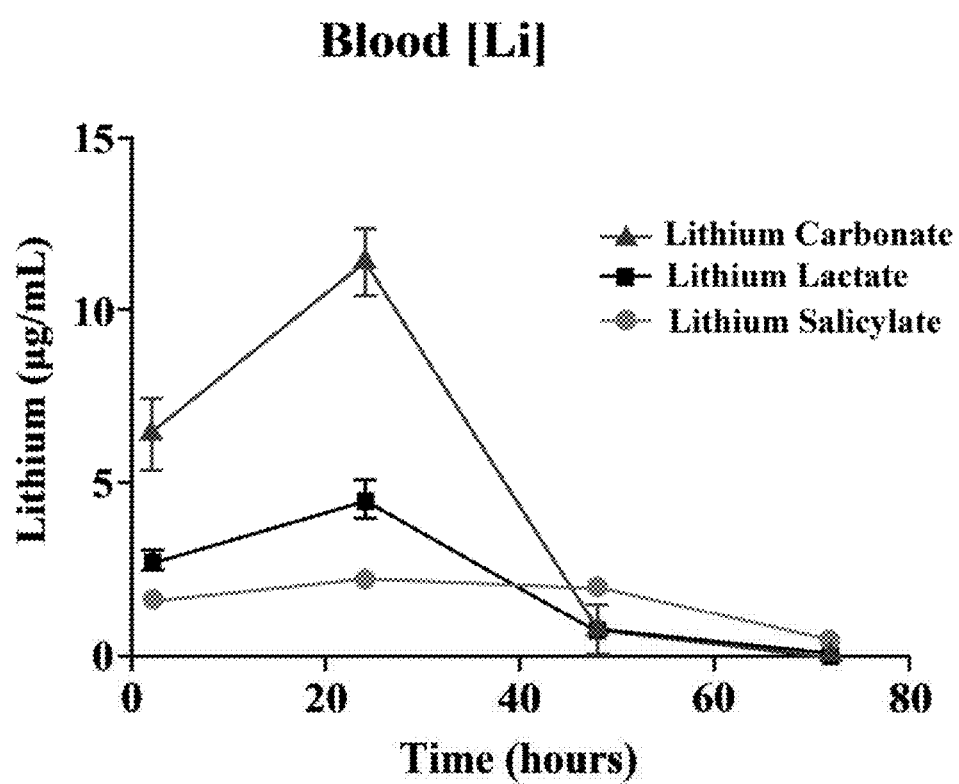
FIG. 3 is a graph showing plasma pharmacokinetics curves of lithium after administration of lithium lactate, lithium salicylate, or lithium carbonate, plotted as mean±SEM ($*p<0.05$, $p<0.01$, $*p<0.001$).

Lithium lactate resulted in elevated lithium plasma levels at 2 hours but peaked at 24 hours post-dose, as seen in FIG. 2. In contrast, lithium salicylate produced elevated lithium plasma levels through the first 48 hours, with peak levels occurring around 48 hours. Lithium carbonate, as a lithium compound approved by the FDA for treatment of mental illnesses, was compared to lithium lactate and salicylate. Similarly to lithium lactate, lithium carbonate peaked at 24 hours, but with levels about 2.5 times that of lithium lactate, about 12 µg/ml, as seen in FIG. 3. Moreover, lithium lactate and lithium carbonate were both eliminated rapidly, having low levels of about 0.5 µg/ml by 48 hours and negligible levels around 0 µg/ml by 72 hours. Levels of lithium salicylate slowly decreased by 48 hours, from 2.1 µg/ml to 2.0 µg/ml, followed by subsequent decrease to low levels of about 0.25 µg/ml by 72 hours. This indicates that lithium salicylate does not result in large fluctuations in lithium concentrations during acute administration of the compound.

Figure 4:
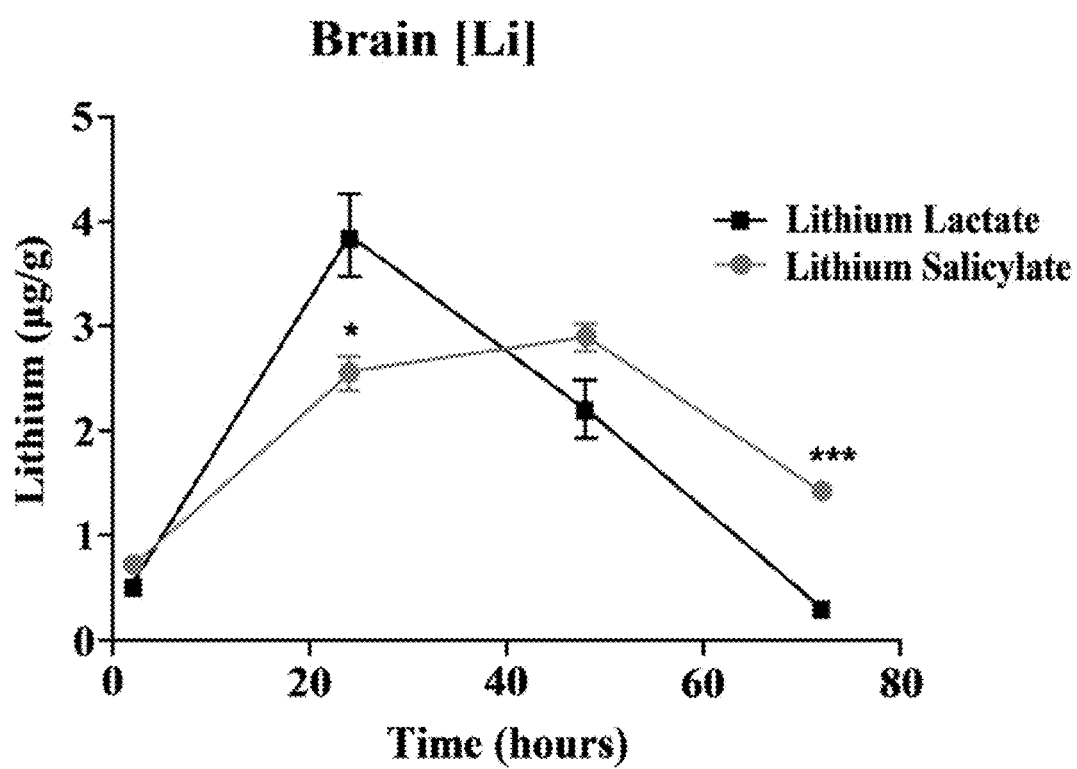
FIG. 4 is a graph showing pharmacokinetics curves of lithium after administration of lithium lactate or lithium salicylate plotted as mean±SEM ($*p<0.05$, $p<0.01$, $*p<0.001$).
Figure 5:
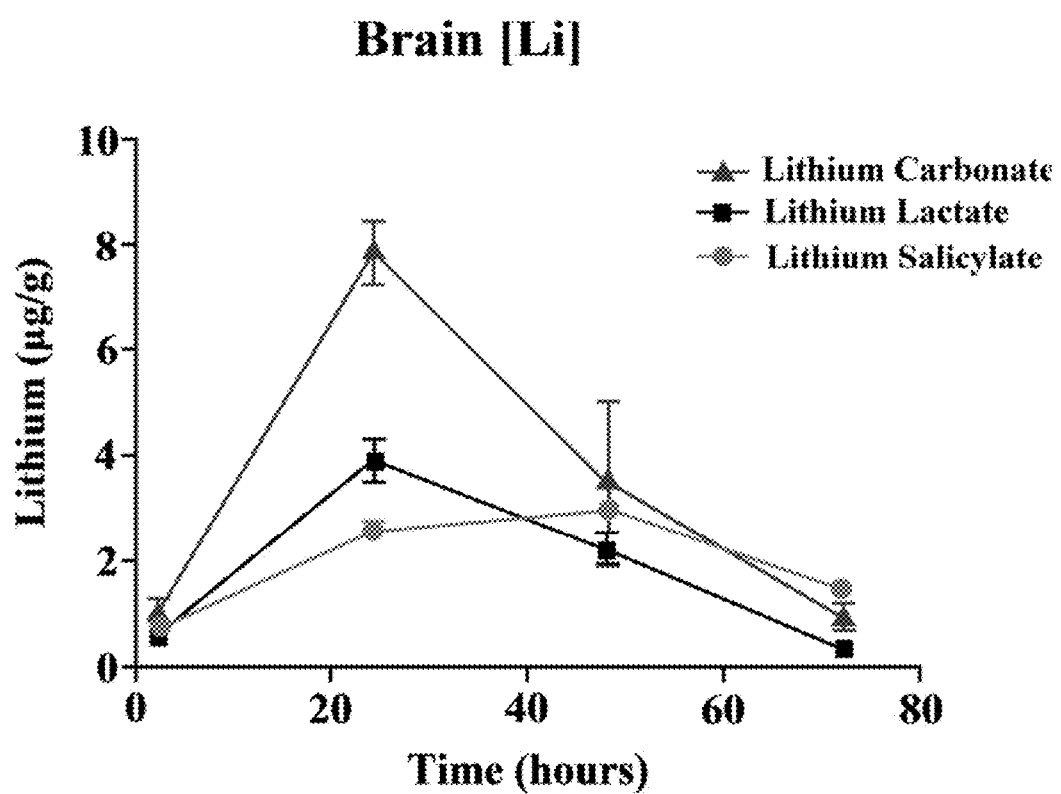
FIG. 5 is a graph showing neuronal pharmacokinetics curves of lithium after administration of lithium lactate or lithium salicylate plotted as mean±SEM ($*p<0.05$, $p<0.01$, $*p<0.001$).

Lithium lactate produced brain levels of lithium that peaked at around 4 µg/ml at 24 hours, whereas and lithium salicylate exhibited peak brain lithium levels of about 2.5 µg/ml at 24 hours and peak lithium levels of 3 µg/ml at 48 hours, as seen in FIG. 4. Further, after peak lithium levels, lithium lactate was quickly removed from the brain, to negligible levels by 72 hours. By comparison, lithium salicylate levels were still at 2 µg/ml by 72 hours. Comparing lithium lactate and lithium salicylate to lithium carbonate showed peak lithium levels of 8 µg/ml at 24 hours, followed by a rapid removal of lithium from the brain, to about 3.8 µg/ml by 48 hours and about 0.5 µg/ml by 72 hours. As seen in FIG. 5, lithium carbonate resulted in significantly higher peak lithium levels in the brain, followed by rapid elimination from the brain. Thus, lithium salicylate exhibited steady pharmacokinetics in the brain throughout the acute administration, with reduced peak levels and lithium levels that persist for longer periods of time in the brain. Lithium salicylate exhibited an unexpected a pharmacokinetic profile that is unlike any other lithium salt therapeutics thus far, namely that lithium salicylate blood/plasma distribution is essentially the same as the brain distribution.

Previous reports show lithium carbonate peaks rapidly and is eliminated within 48 hours (Smith et al., Reinventing lithium therapeutics by crystal engineering of novel ionic cocrystals. Mol Pharm. 2013 Dec. 2; 10(12):4728-38). These pharmacokinetics, i.e. rapid drug peaks followed by rapid elimination, can exacerbate the known toxicity issues of FDA-approved lithium salts, especially given the narrow therapeutic window of lithium-based pharmaceutics. Comparatively, lithium salicylate and lithium lactate underperformed in oral bioavailability as compared to lithium carbonate. However, as oral bioavailability is not a problem with lithium therapeutics this should not disqualify either of these salts for development as drugs. The blood area under curve (AUC) for lithium lactate was higher than lithium salicylate, whereas the brain AUC for lithium salicylate was slightly higher than lithium lactate, as seen in Table 1. Moreover, the plateau plasma levels observed for lithium salicylate indicate the compound has enhanced safety in lithium therapy and, consequently, improve patient compliance. This is supported by previous investigators who suggested that an ideal lithium preparation would attenuate high blood level peaks and exhibit gradually declining blood concentrations (Lippmann S, Evans R 1983. A comparison of three types of lithium release preparations. Hosp Community Psychiatry. 1983 February; 34(2):113-4). Encouragingly, this is precisely the pharmacokinetic profile that was produced by lithium salicylate, as seen in FIGS. 2-5. It was also found that although lithium salicylate produced comparatively lower blood lithium exposure than lithium lactate, it produced better brain exposure. Thus, biodistribution also appears to be affected by the choice of anion.

As shown herein, some currently available but understudied lithium salts (e.g. lithium salicylate) address the toxicity issues associated with conventional lithium salts (lithium carbonate and lithium citrate). Without being limited to a specific theory, the compounds modulating peak lithium levels and lithium low levels over a period of 3 days, reducing chances of a patient reaching toxic levels of lithium. Further, the apparent terminal half-life was longer for lithium salicylate in both the brain and blood. Additionally, as the compounds are not eliminated as rapidly as convention lithium salts, patients stay within a therapeutic window for longer periods of time and require less frequent dosing of lithium. This may also result in less stringent requirements for blood monitoring by a clinician.

EXAMPLE 2

Cocrystals are solids that are crystalline single phase materials composed of two or more different molecular and/or ionic compounds (i.e. cocrystal precursors) generally in a stoichiometric ratio. When one or both of the cocrystal precursors are ionic (i.e., salts), the resulting cocrystal is an ionic cocrystal; when both of the cocrystal precursors are molecular (i.e., molecules including zwitterionic molecules), the resulting cocrystal is a molecular cocrystal. Cocrystals of lithium salts are attractive pharmaceuticals, as the compounds can offer improved efficacy due to rational cocrystal selection that permits the precursors to act synergistically (See, Braga et al., Combining piracetam and lithium salts: ionic co-crystals and co-drugs? Chem Commun (Camb). 2012 Aug. 25; 48(66):8219-21; Wouters, et al., Novel Pharmaceutical Compositions through Co-crystallization of Racetams and Li+ Salts. Cryst Eng Comm. 2013 Aug. 2, 15:8898-8902).

The problems associated with lithium use, as discussed in the background, arise because the site of action for the treatment of psychiatric and neurodegenerative diseases are in the brain and lithium salts cross the blood-brain-barrier slowly (Davenport V D. Distribution of parenterally administered lithium in plasma, brain and muscle of rats. Am J Physiol. 1950; 163:633-41; Ebadi M S, Simmons V J, Hendrickson M J, Lacy P S. Pharmacokinetics of lithium and its regional distribution in rat brain. Eur J Pharmacol. 1974; 27:324-9). Cocrystal forms may exist for an active pharmaceutical ingredient and it may therefore be possible to exert control over solubility to attenuate serum concentration and increase bioavailability (Smith, A. J.; Kavuru, P.; Wojtas, L.; Zaworotko, M. J.; Shytle, R. D. "Cocrystals of Quercetin with Improved Solubility and Oral Bioavailability." Molecular Pharmaceutics, 8, 1867-1876, 2011). Ionic cocrystals of lithium salts with compounds known to be actively transported into the cerebrospinal compartment could preferentially distribute lithium to the brain. Ionic cocrystals of NaCl and sucrose were isolated in the late 1940s (Beevers & Cochran, X-ray examination of sucrose. Nature. 1946 Jun. 29; 157:872).

An important step in the crystal engineering of ionic cocrystals of lithium is the selection of the most appropriate parent lithium salt. One obvious and already identified consideration is that the anion of the lithium salt should be pharmaceutically acceptable (Smith et al., Reinventing lithium therapeutics by crystal engineering of novel ionic cocrystals. Mol Pharm. 2013 Dec. 2; 10(12):4728-38). However, another important factor is pharmacokinetics.

Cocrystals of lithium salicylate and 4-hydroxy proline were formed in a 1:1 molar ratio. Lithium hydroxide (>98%, anhydrous, used as received from Sigma Aldrich, 23.9 mg, 1.0 mmol), salicylic acid (>99% used as received from Sigma Acros Organics, 138.1 mg, 1.0 mmol) and 4-hydroxy proline (99+% pure, used as received from Aldrich, 131.1 mg, 1.0 mmol)) were dissolved in 3.0 mL of deionized water. The solution was evaporated on a hot plate until crystals emerged from solution. Colorless plates (226.0 mg) were collected from the hot solution.

Figure 6:
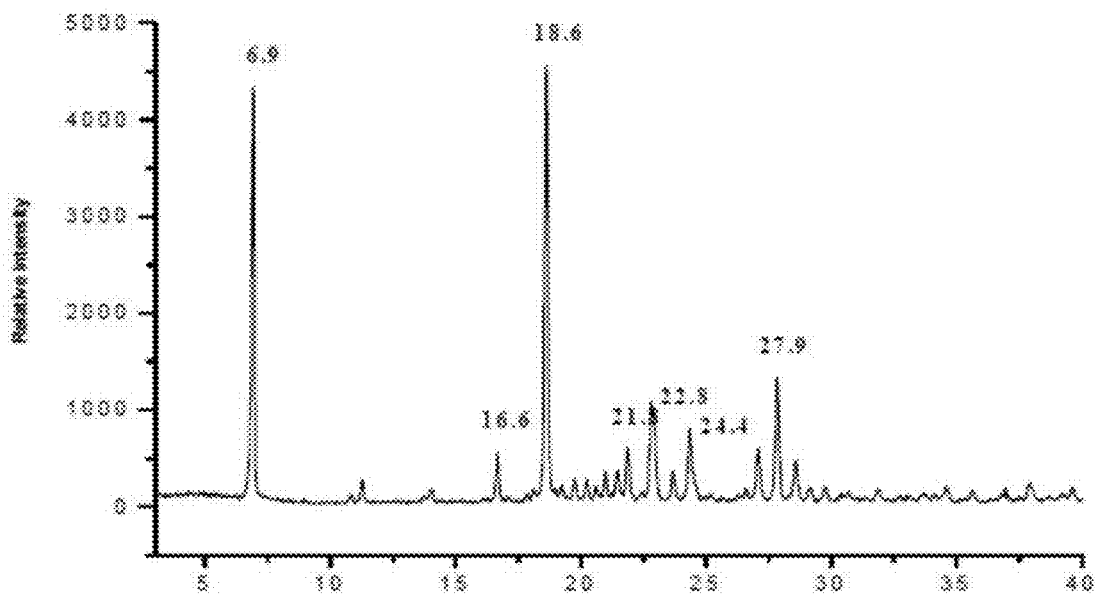
FIG. 6 is the experimental powder x-ray diffraction pattern of LiS₄HPr cocrystals.
Figure 7:
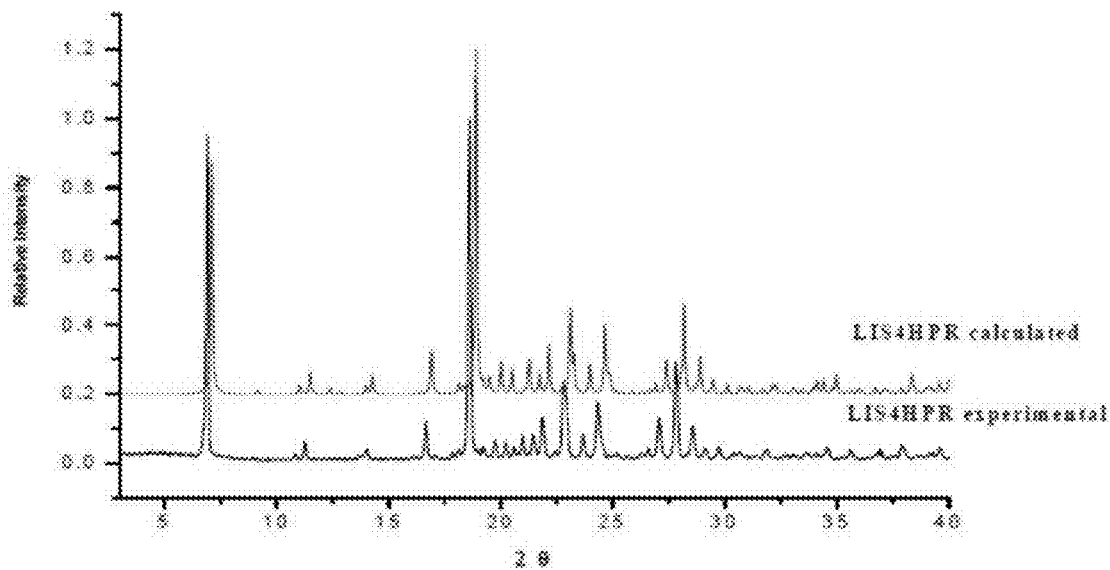
FIG. 7 is a comparison of the calculated and experimental powder x-ray diffraction patterns of LiS₄HPr cocrystals.

Crystals of lithium salicylate and 4-hydroxy proline (LiS$_4$HPr) were characterized by single crystal x-ray crystallography, seen in Table 2, and powder x-ray diffraction (Bruker D8 advance, Cu radiation). As can be seen from FIG. 6, major peaks lie at about the following positions: 6.9, 16.6, 18.6, 21.8, 22.8, 24.4 and 27.9. The single crystal x-ray structure reveals that LiS$_4$HPr is a 1:1 cocrystal of lithium salicylate and 4-hydroxy proline. Each unit cell contains eight salicylate anions, eight hydroxy prolines and eight lithium cations. Each lithium cation is bridged by four carboxylate moieties (two 4-hydroxy prolines and two salicylate anions) to form square grids. As can be seen from the powder x-ray diffraction, major peaks lie at about the following positions: 6.9, 16.6, 18.6, 21.8, 22.8, 24.4 and 27.9, as seen in FIG. 6. Overlaying the experimental and calculated powder x-ray diffraction patterns of LiS$_4$HPr shows that the cocrystals obtained from the methods described herein produced the expected LiS$_4$HPr composition, as seen in FIG. 7. The crystals formed as lithium centers with four salicylate moieties associated with each lithium core and a proline associated with each of the salicylate moieties.

TABLE 2

Single crystal X-ray diffraction data for LiS₄HPr captured by a Bruker-D8 venture photon diffractometer.

Crystallographic data

| | |
|---|---|
| Empirical formula | $C_{12}H_{14}LiNO_6$ |
| Formula weight | 275.18 |
| Temperature | 100 (2) K |
| Wavelength | 1.54178 Å |
| Crystal system | Orthorhombic |
| Space group | $P2_12_12_1$ |
| Unit cell dimensions | a = 9.7805 (5) Å   $\alpha = 90°$ |
| | b = 10.4758 (5) Å  $\beta = 90°$ |
| | c = 24.8959 (12) Å  $\gamma = 90°$ |
| Volume | 2550.8 (2) Å³ |
| Z | 8 |
| Density (calculated) | 1.433 Mg/m3 |
| Reflections collected | 40970 |
| Independent reflections | 4351 [R(int) = 0.0546] |
| Final R indices [I>2sigma(I)] | R1 = 0.0385, wR2 = 0.0809 |
| R indices (all data) | R1 = 0.0455, wR2 = 0.0839 |

EXAMPLE 3

Cocrystals, as discussed in Example 2, were formed from lithium salicylate and beta alanine (LiSBAl) were formed in a 1:1 molar ratio. Lithium hydroxide (>98%, anhydrous, used as received from Sigma Aldrich, 23.9 mg, 1.0 mmol), Salicylic acid (>99% used as received from Sigma Acros Organics, 138.1 mg, 1.0 mmol) and beta alanine (99+% pure, used as received from Aldrich, 178.1 mg, 2.0 mmol)) were dissolved in 5.0 mL of deionized water. The solution was evaporated on a hot plate until crystals emerged from solution. Colorless plates (85.0 mg) were collected from the hot solution.

Figure 8:
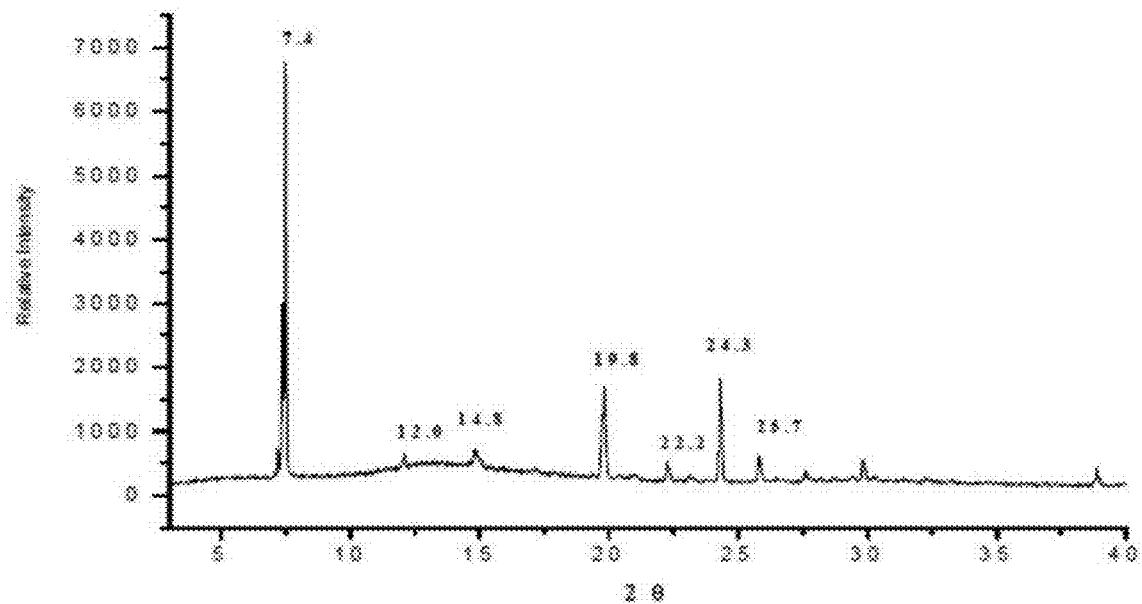
FIG. 8 is the experimental powder x-ray diffraction pattern of LiSBAl cocrystals.

Crystals of LiSBAl were characterized by single crystal x-ray crystallography, as seen in Table 3, and powder x-ray diffraction (Bricker D8 advance, Cu radiation). Single crystal x-ray crystallography exhibited major peaks lie at about the following positions: 7.4, 12.0, 15.0, 19.8, 22.3, 24.5 and 25.8, as seen in FIG. 8.

Figure 9:
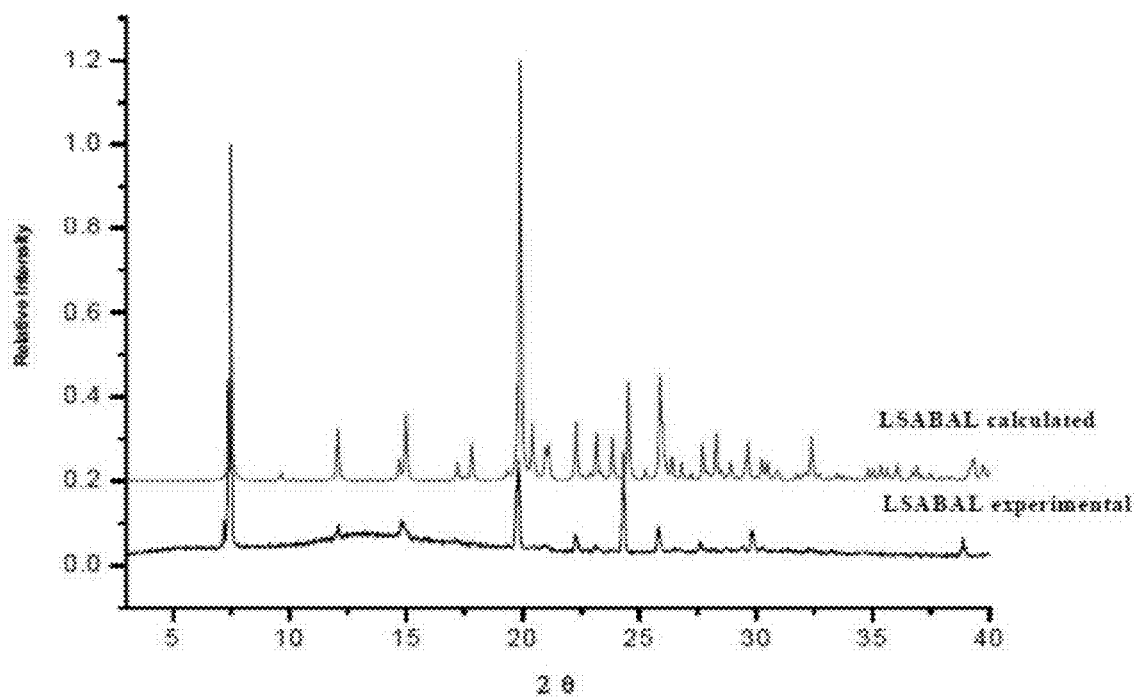
FIG. 9 is an overlay of the calculated and experimental powder x-ray diffraction patterns of LiSBAl for comparison.

As in the previous example, a comparison of experimental and calculated powder x-ray diffraction patterns of LiSBAl showed substantial overlap between the graphs and indicated that the cocrystals obtained from the methods described herein produced the expected 1:1 cocrystal of lithium salicylate and beta alanine, as seen in FIG. 9. Each lithium cation is bridged by four carboxylate moieties, two from beta alanine (Li—O bond distances: 1.920 Å, 1.923 Å) and two from salicylate anions (Li—O bond distances: 1.921 Å, 1.939 Å) to form a square grid.

TABLE 3

Single crystal X-ray diffraction data for LiSBAl, captured by a Bruker-D8 venture photon diffractometer.

Crystallographic data

| | |
|---|---|
| Empirical formula | $C_{20}H_{24}Li_2N_2O_{10}$ |
| Formula weight | 466.29 |
| Temperature | 120(2) K |
| Wavelength | 1.54178 Å |
| Crystal system | Orthorhombic |
| Space group | $P2_12_12_1$ |
| Unit cell dimensions | a = 9.3574(6) Å   $\alpha = 90°$ |
| | b = 9.9529(6) Å   $\beta = 90°$ |
| | c = 23.5985(15) Å  $\gamma = 90°$ |
| Volume | 2197.8(2) Å³ |
| Z | 4 |
| Density (calculated) | 1.409 mg/m3 |
| Reflections collected | 30531 |
| Independent reflections | 3692 [R(int) = 0.0543] |
| Final R indices [I>2sigma(I)] | R1 = 0.0261, wR2 = 0.0607 |
| R indices (all data) | R1 = 0.0286, wR2 = 0.0620 |

EXAMPLE 4

Cocrystals, as discussed in Example 2, were formed from lithium salicylate and L proline (LiSPro) were formed in a 1:1 molar ratio. Lithium Salicylate (99+%, anhydrous, used as received from Sigma Aldrich, 1 mmol) and L-proline (99+% pure, used as received from Sigma Aldrich, 1 mmol) were dissolved in 2.0 ml of hot deionised water. It was maintained on the hot plate (75-90° C.) until crystal formation. Colorless crystals (approximately 218 mg) were collected.

Crystals of LiSPro were characterized by FT-IR spectroscopy (Nicolet Avatar 320 FTIR, solid state), DSC (TA instrument 2920), powder x-ray diffraction (Bruker AXS D8, Cu radiation) and single crystal x-ray crystallography.

Figure 10:
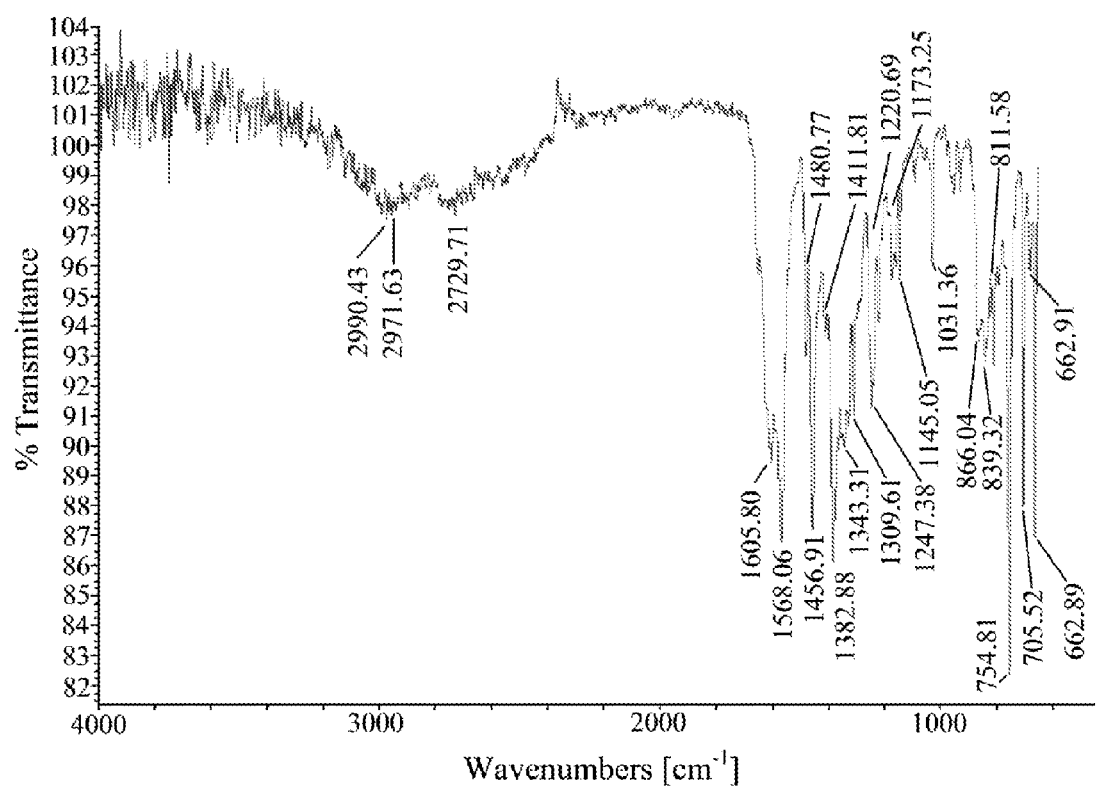
FIG. 10 is a FT-IR diagram of LiSPro cocrystals.
Figure 11:
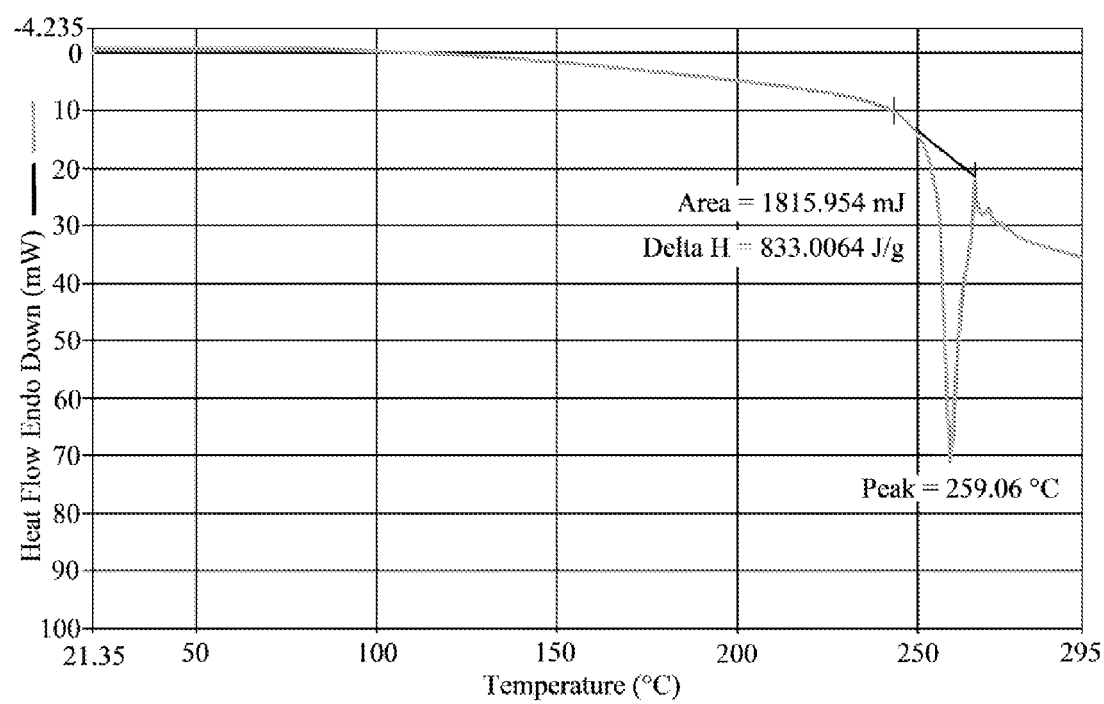
FIG. 11 is a DSC diagram of LiSPro cocrystals.

FT-IR spectroscopy as seen in FIG. 10 shows peaks at 1670, showing unsaturation of the compound, as well as peaks at 1459, and 2700 and 2900, found in a broad peak spanning from about 2600 to 3100. Differential scanning calorimetry (DSC) showed a peak at 260° C., as seen in FIG. 11, indicating the cocrystals began melting. Powder x-ray diffraction showed major peaks were observed in the calculated powder x-ray diffraction pattern at approximately the following positions: 7.2, 11.3, 17.1, 18.6, 19.4, 20.9, 22.8, 24.7, 28.2°. Data from the single crystal x-ray crystallography are shown in Table 4, and reveals that LiSPro contains four lithium cations, four salicylate anions and four L-proline molecules in the unit cell. Each lithium cation is stabilized by tetrahedral coordination in square grid type waved 2-D layers extended in a and b directions. In the c direction, the layers are held together through pi-pi and CH-pi interaction of aromatic rings as well as weak CH—O interactions.

TABLE 4

Single crystal x-ray diffraction data for LISPRO (Bruker-AXS APEX2 CCD diffractometer)

Crystallographic data

| | |
|---|---|
| Empirical formula | $C_{24}H_{25}Li_2N_2O_{10}$ |
| Formula weight | 515.34 |
| Temperature | 293(2) K |
| Wavelength | 1.54178 Å |
| Crystal system | Monoclinic |
| Space group | $P 2_1$ |
| Unit cell dimensions | a = 10.3591(16) Å  $\alpha = 90.00°$ |
| | b = 10.1545(14) Å  $\beta = 93.460 (10)$ |
| | c = 12.173(2) Å  $\gamma = 90.00°$ |
| Volume | 1278.2 (4) Å³ |
| Z | 2 |
| Density (calculated) | 1.339 Mg/m³ |
| Reflections collected | 5567 |
| Independent reflections | 3498 [R(int) = 0.0431] |
| Final R indices [I>2sigma(I)] | R1 = 0.0976, wR2 = 0.2651 |
| R indices (all data) | R1 = 0.1439, wR2 = 0.3124 |

EXAMPLE 5

2:1 cocrystals of amino acids and lithium salts therefore can be prepared that possess a dia and/or zeolitic framework. However, a structural feature of zeolites is the presence of one or more rings.

A series of 2:1 amino acid (sarcosine, SAR, N,N-dimethylglycine DMG, betaine, BTN and L-proline, PRO) cocrystals of lithium salts (lithium chloride, LIC, lithium bromide, LIB and lithium nitrate, LIN) were previously prepared possessing a stoichiometry permitting such structure formation. These cocrystals were prepared by slow evaporation of aqueous solutions of LIC, LIB or LIN and two equivalents of the amino acid at around 80° C. (See, Zaworotko, et al., U.S. application Ser. No. 14/007,023, herein incorporated by reference).

Lithium bromide, anhydrous (99% pure, used as received from Acros Organics, 1 g, 1 1.5 mmol) and L-proline (99-F % pure, used as received from Aldrich, 1.33 g, 11.5 mmol) were dissolved in 2.0 ml of hot deionized water. The solution was maintained on the hot plate until crystals emerged from the hot solution. The conditions provided can be used produce cocrystals of lithium salicylate and an amino acid having the properties described in Zaworotko, et al. (U.S. application Ser. No. 14/007,023). For example, use of an anionic lithium salt, such as lithium hydroxide (>98%, anhydrous, used as received from Sigma Aldrich, 23.9 mg, 1.0 mmol), with salicylic acid (>99% used as received from Sigma Acros Organics, 138.1 mg, 1.0 mmol) and an amino acid can be combined in a 1:1:2 molar ratio of lithium salt:salicyclic acid:amino acid in deionized water and heated until crystals precipitated. Alternatively, lithium salicylate (99+%, anhydrous, used as received from Sigma Aldrich, 1 mmol) and an amino acid can be dissolved in deionized water and heated until crystals precipitated.

All referenced publications are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method for treating a neurological disorder comprising: administering a therapeutically effective amount of a composition to a patient in need thereof, wherein the composition comprises lithium salicylate or lithium lactate in non-cocrystalized form; and wherein the neurological disorder is bipolar disorder, acute mania, manic depression, schizophrenia, anorexia, bulimia, Tourette's syndrome, cyclical vomiting, paresthesias, or aggressive behavior in attention deficit hyperactivity disorder.

2. The method of claim 1, wherein the composition is administered 48 hours apart.

3. The method of claim 1, wherein the composition is administered 72 hours apart.

4. The method of claim 1, wherein the composition is administered at between 15 mg/kg/day and 200 mg/kg/day.

5. The method of claim 2, wherein the composition is administered at between 30 mg/kg/dose every other day to 400 mg/kg/dose every other day.

6. The method of claim 1, wherein the composition is administered at between 15 mg/kg/day to 100 mg/kg/day.

7. The method of claim 2, wherein the composition is administered at between 30 mg/kg/dose every other day to 200 mg/kg/dose every other day.

8. A method for treating a neurological disorder comprising:
administering a therapeutically effective amount of a composition to a patient in need thereof, wherein the composition comprises lithium lactate in non-cocrystalized form; and wherein the neurological disorder is bipolar disorder, acute mania, manic depression, schizophrenia, anorexia, bulimia, Tourette's syndrome, paresthesias, aggressive behavior in attention deficit hyperactivity disorder, Huntington's disease, or tardive dyskinesia.

9. The method of claim 8, wherein the composition is administered at least 24 hours apart.

10. The method of claim 8, wherein the composition is administered 48 hours apart.

11. The method of claim 8, wherein the composition is administered 72 hours apart.

12. The method of claim 8, wherein the composition is administered at between 15 mg/kg/day and 200 mg/kg/day.

13. The method of claim 10, wherein the composition is administered at between 30 mg/kg/dose every other day to 400 mg/kg/dose every other day.

14. The method of claim 8, wherein the composition is administered at between 15 mg/kg/day to 100 mg/kg/day.

15. The method of claim 10, wherein the composition is administered at between 30 mg/kg/dose every other day to 200 mg/kg/dose every other day.

* * * * *